US00PP15541P2

(12) United States Plant Patent
Pierce

(10) Patent No.: US PP15,541 P2
(45) Date of Patent: Feb. 8, 2005

(54) ***ANTIRRHINUM* PLANT NAMED 'SULTE LITYEL'**

(50) Latin Name: *Antirrhinum×hybrida*
Varietal Denomination: Sulte Lityel

(75) Inventor: Robert Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 7 days.

(21) Appl. No.: 10/818,360

(22) Filed: Apr. 5, 2004

(51) Int. Cl.[7] ..... A01H 5/00
(52) U.S. Cl. ..... Plt./322
(58) Field of Search ..... Plt./322

*Primary Examiner*—Kent Bell
(74) *Attorney, Agent, or Firm*—C. A. Whealy

(57) ABSTRACT

A new and distinct cultivar of *Antirrhinum* plant named 'Sulte Lityel', characterized by its outwardly spreading, decumbent and mounded plant habit; freely branching habit; freely flowering habit; and numerous flowers that are light yellow in color.

1 Drawing Sheet

Botanical classification/cultivar designation: *Antirrhinum×hybrida* cultivar Sulte Lityel.

BACKGROUND OF THE INVENTION

The present Invention relates to a new and distinct cultivar of *Antirrhinum* plant, commercially known as a trailing Snapdragon, botanically known as *Antirrhinum hybrida,* and hereinafter referred to by the cultivar name Sulte Lityel.

The new *Antirrhinum* is a product of a planned breeding program conducted by the Inventor in Gilroy, Calif. The objective of the breeding program is to create new early and freely flowering *Antirrhinums* with trailing and mounded plant habit and attractive leaf and flower coloration.

The new *Antirrhinum* originated from a cross-pollination made by the Inventor in September, 2000 of a proprietary selection of *Antirrhinum hybrida* identified as code number 17-1, not patented, as the female, or seed parent, with a proprietary selection of *Antirrhinum hybrida* identified as code number 57-1, not patented, as the male, or pollen parent. The new *Antirrhinum* was selected as a single plant from the resulting progeny of the cross-pollination in a controlled environment in Gilroy, Calif. in May, 2001.

Asexual reproduction of the new cultivar by terminal vegetative cuttings since May, 2001, in Gilroy, Calif. has shown that the unique features of this new *Antirrhinum* are stable and reproduced true to type in successive generations.

SUMMARY OF THE INVENTION

Plants of the cultivar Sulte Lityel have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Sulte Lityel'. These characteristics in combination distinguish 'Sulte Lityel' as a new and distinct cultivar:

1. Outwardly spreading, decumbent and mounded plant habit.
2. Freely branching habit.
3. Freely flowering habit.
4. Numerous flowers that are light yellow in color.

In side-by-side comparisons conducted in Gilroy, Calif., plants of the new *Antirrhinum* differed from plants of the female parent selection in the following characteristics:

1. Plants of the new *Antirrhinum* were not as upright as plants of the female parent selection.
2. Plants of the new *Antirrhinum* flowered earlier than plants of the female parent selection.
3. Plants of the new *Antirrhinum* and the female parent selection differed in flower color as plants of the female parent selection had bronze-colored flowers.

In side-by-side comparisons in Gilroy, Calif., plants of the new *Antirrhinum* differed from plants of the male parent selection in the following characteristics:

1. Plants of the new *Antirrhinum* had larger leaves than plants of the male parent selection.
2. Plants of the new *Antirrhinum* flowered earlier than plants of the male parent selection.
3. Plants of the new *Antirrhinum* and the male parent selection differed in flower color as plants of the male parent selection had red-colored flowers.

Plants of the new *Antirrhinum* can be compared to plants of the cultivar Luminaire Yellow, not patented. In side-by-side comparisons conducted in Gilroy, Calif., plants of the new *Antirrhinum* differed from plants of the cultivar Luminaire Yellow in the following characteristics:

1. Plants of the new *Antirrhinum* had smaller leaves than plants of the cultivar Luminaire Yellow.
2. Flowers of plants of the new *Antirrhinum* were lighter yellow in color than flowers of plants of the cultivar Luminaire Yellow.
3. Plants of the new *Antirrhinum* had broader sepals than plants of the cultivar Luminaire Yellow.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Antirrhinum.*

The photograph at the top of the sheet comprises a side perspective view of a typical plant of 'Sulte Lityel' grown in a container.

The photograph at the bottom of the sheet is a close-up view of typical flowers and leaves of 'Sulte Lityel'.

DETAILED BOTANICAL DESCRIPTION

Plants of the cultivar Sulte Lityel have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a polyethylene-covered greenhouse during the summer with day temperatures ranging from 24 to 29° C., night temperatures ranging from 13 to 18° C. and light levels about 2,000 foot-candles. Plants used for the photographs and description were about 12 weeks from planting rooted cuttings. In the following description, color references are made to The Royal Horticultural Society Colour Chart, 1995 Edition, except where general terms of ordinary dictionary significance are used.

Botanical classification: *Antirrhinum hybrida* cultivar Sulte Lityel.

Parentage:

*Female parent.*—Proprietary selection of *Antirrhinum hybrida* identified as code number 17-1, not patented.

*Male parent.*—Proprietary selection of *Antirrhinum hybrida* identified as code number 57-1, not patented.

Propagation:

*Type cutting.*—Terminal vegetative cuttings.

*Time to initiate roots, summer and winter.*—About 12 to 16 days at 21 to 23° C.

*Time to develop roots, summer and winter.*—About 25 to 30 days at 21 to 23° C.

*Root description.*—Fine, fibrous; white in color.

*Rooting habit.*—Freely branching.

Plant description:

*Form.*—Annual flowering plant; initially upright, then low trailing and outwardly spreading; decumbent; uniformly mounded plant form. Freely branching habit; about eight basal branches per plant. Pinching enhances development of lateral branches.

*Usage.*—Appropriate for hanging baskets, window boxes, patio containers and landscape applications.

*Plant height.*—About 13 cm.

*Plant diameter* (*area of spread*).—About 38 cm.

*Vigor.*—Moderately vigorous; moderate growth rate.

*Lateral branches.*—Length: About 23 cm. Diameter: About 2 mm. Internode length: About 2 cm. Texture: Sparsely pubescent. Color: 146B.

*Foliage description.*—Arrangement: Opposite before flowering; alternate after flowers develop; simple. Length: About 4.2 cm. Width: About 1.4 cm. Shape: Elliptic. Apex: Broadly acute. Base: Attenuate. Margin: Entire. Texture, upper and lower surfaces: Smooth, glabrous. Venation pattern: Pinnate, arcuate. Color: Developing and fully expanded leaves, upper surface: 147A. Developing and fully expanded leaves, lower surface: 147B. Venation, upper and lower surfaces: 147B. Petiole length: About 8 mm. Petiole diameter: About 1 mm. Petiole color, upper and lower surfaces: 146B.

Flower description:

*Flower type and habit.*—Single bi-labiate flowers arranged on terminal racemes; flowers opposite. Freely flowering habit, usually about eight open flowers and about four flower buds per raceme. Flowers face outwardly. Flowers not persistent. Flowers not fragrant.

*Natural flowering season.*—Long flowering period, spring until autumn; flowering continuous during this period. Plants start flowering about eight weeks after planting rooted cuttings.

*Flower longevity.*—Flowers last about one week on the plant.

*Flower length.*—About 3 cm.

*Flower width.*—About 2.4 cm.

*Flower depth.*—About 3.7 cm.

*Flower buds.*—Length: About 1.1 cm. Diameter: About 8 mm. Shape: Ovoid. Color: 1C.

*Corolla.*—Shape/arrangement: Broadly tubular; five modified petals; upper two and lower three petals fused. Petal lobe apices: Rounded. Petal lobe margin: Entire, slightly serrate. Length, upper petal lobes: About 2.5 cm. Length, lower petal lobes: About 1.7 cm. Width, upper petal lobes: About 1.5 cm. Width, lower petals lobes: About 1.1 cm. Texture, upper and lower surfaces of petal lobes: Pubescent; velvety. Texture, throat: Pubescent. Color: When opening, upper petal lobes, upper surface: 4C. When opening, lower petal lobes, upper surface: 4C; palate, 4A; at the throat, 5A. When opening, all petal lobes, lower surface: 4D. Fully opened, upper petal lobes, upper surface: 4C; towards the throat, 4D. Fully opened, lower petal lobes, upper surface: 4C; palate, 4A; at the throat, 5C. Fully opened, all petal lobes and tube, lower surface: 4D.

*Sepals.*—Quantity/arrangement: Five per flower; fused at base. Length: About 6 mm. Width: About 3 mm. Shape: Elliptic. Apex: Acute. Margin: Entire. Texture, upper and lower surfaces: Densely pubescent. Color, upper and lower surfaces: 147B.

*Pedicels.*—Length: About 1 cm. Diameter: About 1 mm. Strength: Strong; flexible. Angle: About 45° from the stem. Color: 146D.

*Reproductive organs.*—Androecium: Stamen quantity: Four per flower. Anther size: About 2 mm by 3 mm. Anther shape: Oval, bi-lobed. Anther color: 10C. Pollen amount: Moderate. Pollen color: 10A. Gynoecium: Pistil quantity: One per flower. Pistil length: About 1.8 cm. Style length: About 1.5 cm. Style color: 1C to 1D. Stigma color: 145D. Ovary color: 1C.

*Seeds/fruits.*—Seed and fruit development has not been observed.

Disease/pest resistance: Plants of the new *Antirrhinum* have not been observed to be resistant to pathogens and pests common to *Antirrhinum.*

It is claimed:

1. A new and distinct cultivar of *Antirrhinum* plant named 'Sulte Lityel', as illustrated and described.

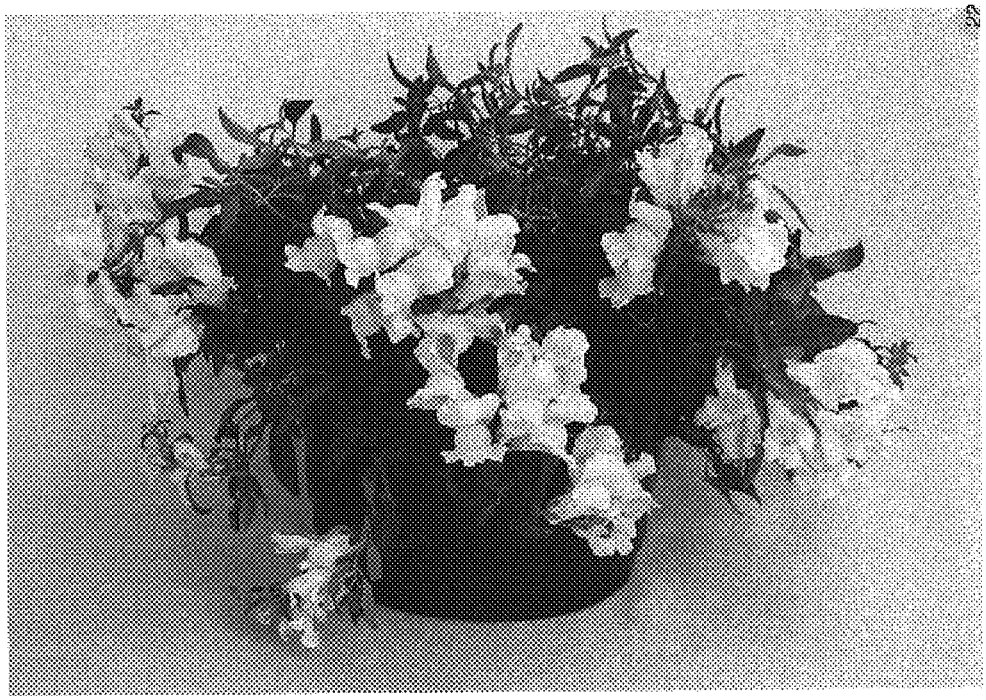
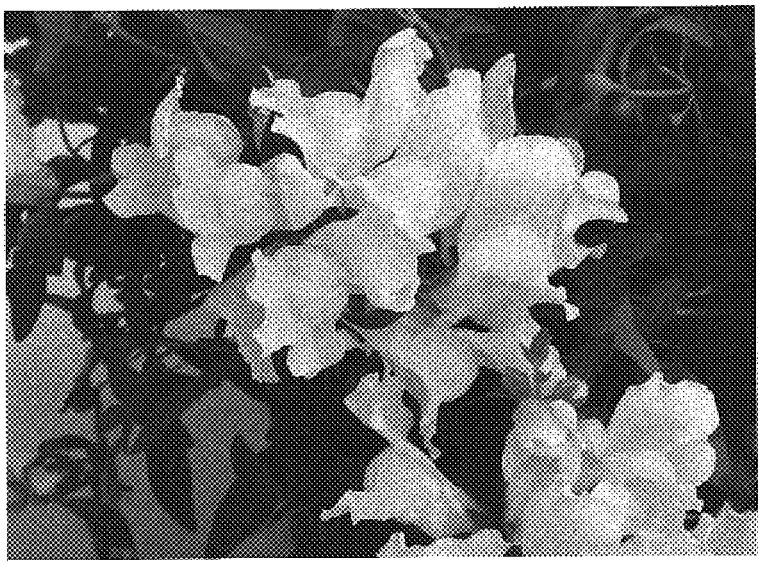

* * * * *